(12) United States Patent
Barre et al.

(10) Patent No.: US 7,795,277 B2
(45) Date of Patent: Sep. 14, 2010

(54) 7-(2-(4-(3-TRIFULOROMETHYL-PHENYL)-1,2,3,6-TETRAHYDROPYRID-1-YL)ETHYL) ISOQUINOLINE BESYLATE SALT, PREPARATION AND THERAPEUTIC USE THEREOF

(75) Inventors: Corinne Barre, Montbazin (FR); Olivier Monnier, Villeveyrae (FR)

(73) Assignee: sanofi-aventis, Paris (FR)

( * ) Notice: Subject to any disclaimer, the term of this patent is extended or adjusted under 35 U.S.C. 154(b) by 541 days.

(21) Appl. No.: 11/853,920

(22) Filed: Sep. 12, 2007

(65) Prior Publication Data
US 2008/0085917 A1  Apr. 10, 2008

Related U.S. Application Data

(63) Continuation of application No. PCT/FR2006/000566, filed on Mar. 15, 2006.

(30) Foreign Application Priority Data
Mar. 17, 2005 (FR) .................... 0502611

(51) Int. Cl.
C07D 401/02 (2006.01)
A61K 31/4709 (2006.01)
(52) U.S. Cl. ...................... 514/307; 546/148
(58) Field of Classification Search ............ None
See application file for complete search history.

(56) References Cited

U.S. PATENT DOCUMENTS 5,981,754 A  11/1999  Baroni
6,509,351 B1  1/2003  Baroni
7,186,720 B2  3/2007  Baroni
2004/0127517 A1  7/2004  Baroni

OTHER PUBLICATIONS

English Translation of International Preliminary Report for PCT/FR06/000566 filed Feb. 10, 2007.*

* cited by examiner

Primary Examiner—Zinna N Davis
(74) Attorney, Agent, or Firm—Ronald G. Ort

(57) ABSTRACT

The present invention relates to the besylate salt of 7-(2-(4-(3-(trifluoromethyl)phenyl)-1,2,3,6-tetrahydropyrid-1-yl)ethyl)isoquinoline, to its preparation and to its use in therapeutics. The salt may be represented by the formula (II) below.

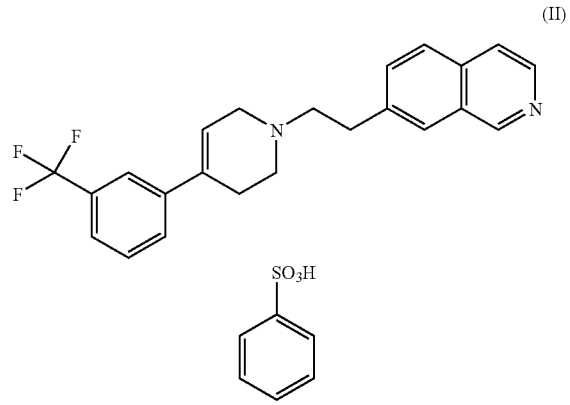

(II)

6 Claims, No Drawings

7-(2-(4-(3-TRIFULOROMETHYL-PHENYL)-1,2,3,6-TETRAHYDROPYRID-1-YL)ETHYL) ISOQUINOLINE BESYLATE SALT, PREPARATION AND THERAPEUTIC USE THEREOF

The invention relates to a novel salt of 7-(2-(4-(3-(trifluoromethyl)phenyl)-1,2,3,6-tetrahydropyrid-1-yl)ethyl)isoquinoline, to its preparation and to its use in therapeutics.

7-(2-(4-(3-(Trifluoromethyl)phenyl)-1,2,3,6-tetrahydropyrid-1-yl)ethyl)isoquinoline, of formula (I) below, is disclosed in the document WO 2001/029026.

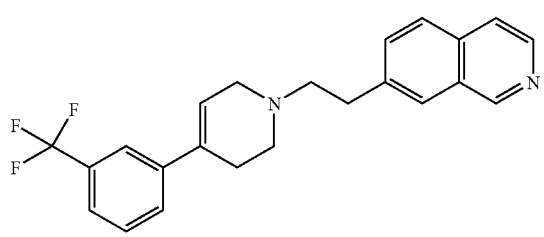
(I)

This compound, among other tetrahydropyridine derivatives, is described as a molecule which modulates the activity of TNF-α (Tumor Necrosis Factor).

The document WO 2001/029026 discloses 7-(2-(4-(3-(trifluoromethyl)phenyl)-1,2,3,6-tetrahydropyrid-1-yl)ethyl)isoquinoline in the free base form or in the form of various salts, such as the dihydrochloride or the fumarate.

It has now been found that the monobenzenesulfonate (also referred to as besylate) salified form of this same compound exhibits advantageous properties which render it particularly suitable for use as active principle in a medicament.

A subject-matter of the invention is thus the besylate salt of 7-(2-(4-(3-(trifluoromethyl)phenyl)-1,2,3,6-tetrahydropyrid-1-yl)ethyl)isoquinoline, its preparation and its application in therapeutics.

The besylate salt of 7-(2-(4-(3-(trifluoromethyl)phenyl)-1,2,3,6-tetrahydropyrid-1-yl)ethyl)isoquinoline is defined in the formula (II) below.

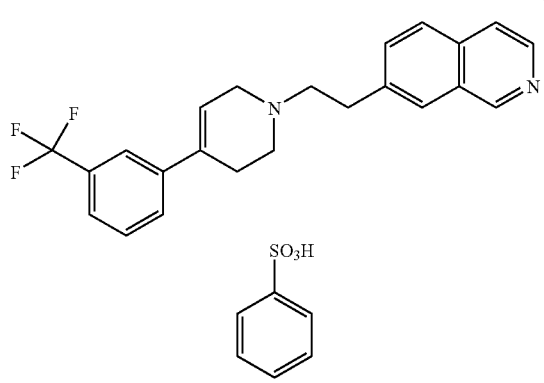
(II)

Specifically, it has been demonstrated, unexpectedly, that the besylate form of the compound of formula (I) has stability properties, in particular with respect to moisture, which are further improved with respect to the dihydrochloride or fumarate form of this same compound.

It has also been demonstrated that the besylate form of the compound of formula (I) additionally has hygroscopicity properties which are improved with respect to the dihydrogensulfate, dibesylate or dihydrochloride forms of this same compound.

In accordance with the invention, the compound of general formula (I) can be prepared according to the process disclosed in Application WO 2001/029026. In that which follows, the starting materials and the reactants, when their preparation is not described, are commercially available or are described in the literature or else can be prepared according to methods which are described therein or which are known to a person skilled in the art.

The advantages related to the besylate form of the compound of formula (I) with respect to the free base form or to other saline forms, such as the dihydrochloride and the fumarate, will emerge from the physicochemical analyses described below.

EXAMPLE 1

Preparation of 7-(2-(4-(3-(trifluoromethyl)phenyl)-1,2,3,6-tetrahydropyrid-1-yl)ethyl)isoquinoline besylate 3.86 g of benzenesulfonic acid are dissolved with stirring at 70° C. in 50 ml of ethanol. 11 g of 7-(2-(4-(3-(trifluoromethyl)phenyl)-1,2,3,6-tetrahydropyrid-1-yl)ethyl)isoquinoline in 60 ml of ethanol are added with stirring to the ethanolic benzenesulfonic acid solution. The solution is subsequently cooled from 70° C. to 20° C. with a temperature gradient of −20° C. per hour.

The precipitate collected is subsequently filtered off, washed twice with 22 ml of ethanol and then dried under vacuum at 50° C.

The title product, with a purity of 99%, is obtained in the form of a white powder.

Yield: 87.3%

M.p.=189.5° C.

$^1$H NMR (303 kHz, $d_4$-methanol) δ (ppm): 2.93 (complex, 2H), 3.35-3.42 (complex, 2H), 3.59-3.64 (complex, 2H), 3.66 (broad t, J=5.13, 2H), 4.08 (broad s, 2H), 6.24 (ddd, J=6.89, 3.46, 1.62, 1H), 7.34 (complex, 2H), 7.37 (complex, 1H), 7.57 (t, J=7.70, 1H), 7.62 (d, J=7.72, 1H), 7.72 (d, J=7.91, 1H), 7.73 (s, 1H), 7.79 (dd, --, 1.72, 1H), 7.81 (dd, 2H), 7.82 (d, J=5.57, 1H), 7.94 (d, J=8.50, 1H), 8.05 (broad s, 1H), 8.42 (d, J=5.82, 1H), 9.20 (s, 1H)

Comparison of the Physicochemical Properties Obtained with Different Salts

EXAMPLE 2

Chemical Stability

The chemical stability of the compound of formula (I) in the dihydrochloride, dihydrogensulfate, fumarate, dibenzenesulfonate and monobenzenesulfonate forms was studied.

Each of the five above salts is exposed to heat, to moisture and to light under the conditions below:

14 days at a temperature of 80° C., 14 days at a temperature of 80° C. and a relative humidity (RH) level of 80%, exposure to light of 400 W.Hrs.m$^{-2}$.

The results, measured by high performance liquid chromatography (HPLC), are given in Table I below.

TABLE I

| Conditions | Salt | | | | |
|---|---|---|---|---|---|
| | Dihydro-chloride | Dihydrogen-sulfate | Fumarate | Dibesylate | Besylate |
| Initial purity | 97.0% | 93.3% | 97.9% | 97.5% | 98.2% |
| 14 days at 80° C. | 95.6% | 91.9% | 96.7% | 97.5% | 97.9% |
| 14 days at 80° C./ 80% RH | 92.9% | 88.5% | 32.4% | 96.2% | 96.5% |

As is apparent, the compound of formula (I) in the besylate form shows a chemical stability towards heat which is among the highest.

The compound (I) in the besylate form is also among the salts the least decomposed during tests carried out at temperature and under humidity.

EXAMPLE 3

Water Content

The water content of the five above salts was studied by thermogravimetric analysis (TGA).

The TGA tests are carried out in a TA8000 device equipped with a TGA850 module. The temperature calibrations are carried out conventionally using the melting of indium.

The experimental parameters employed were:

| Starting temperature: | 25° C. |
|---|---|
| Heating gradient: | 10° C./min |

Final temperature: 250° C. for the dihydrochloride, 300° C. for the fumarate, 200° C. or 250° C. for the dihydrogensulfate, 250° C. or 300° C. for the dibesylate and the besylate.

The system is purged using nitrogen at a flow rate of 70 ml/min.

The pans used were 70 μl silica pans.

The results are given in Table II below.

TABLE II

| Salt | Loss in weight (% weight/weight) | Nature of the solvent |
|---|---|---|
| Dihydrochloride | 11.0 | Water |
| Dihydrogensulfate | 2.06 | Solvent + water |
| Fumarate | 0.45 | Solvent + water |
| Dibesylate | 0.72 | Water |
| Besylate | 0.11 | Water |

The TGA curve of the dihydrochloride shows that the salt comprises three water molecules per mole of anhydrous salt and can be regarded as existing in the trihydrate form. The loss of water appears at a relatively low temperature, which reflects a weakly bonded nature of this hydrate. Such a form can prove to be disadvantageous, it being possible for the stoichiometry to vary according to the ambient conditions. This type of result potentially reflects the probability that the active principle can exist in different hydrated forms.

The fumarate shows a small loss in weight between 25° C. and 110° C. by TGA, which is attributed to residual solvent and to weakly bonded water. Similarly, the dihydrogensulfate and dibesylate exhibit losses in weight by TGA due to residual solvent or weakly bonded water, followed at high temperature by the decomposition of the product.

The dihydrogensulfate and the dibesylate show a significant acquisition of water during the sorption cycle between 30 and 80% relative humidity which it is generally desired to avoid for a pharmaceutical composition. The hystereses observed during the desorption show a change in the physical form of the product studied, which is generally not desired for an active substance.

The DVS tests are carried out using a DVS-1 system. From 20 to 32 mg of product are used per analysis and the temperature is maintained at 25° C. plus or minus 0.2° C. Nitrogen is used as carrier gas at a flow rate of 100 ml/min in the sample chamber. The relative humidity changes according to cycles from 30% to 95%, then to 0%, to terminate at 30%, in increments, when the equilibrium conditions (dm/dt) of 0.0002% are achieved, over a period of 5 min.

The sorption isotherms of the fumarate show that this salt is weakly hygroscopic. The sorption isotherms of the dihydrochloride show that 1.9% weight/weight of water is acquired during the sorption cycle between 30 and 80% relative humidity. This significant sorption remains acceptable, however, all the more so as a weak hysteresis is observed over the entire working range between 20% and 95% RH.

On the other hand, the besylate is not hydrated and shows excellent behavior during the water sorption isotherm measurements. This salt appears to be the least hygroscopic of all the salts tested. No hysteresis is recorded during the DVS measurement in sorption and in desorption, which makes it potentially advantageous for a pharmaceutical development.

It emerges from these analyses that the besylate salt of the compound of formula (I) exhibits both hygroscopicity and stability properties, whether towards dry or wet heat, which are better than those of the other salts tested and which make it particularly suitable for the manufacture of medicaments.

The physicochemical properties of the compound of formula (I) in the besylate form also allow it to be stored under normal conditions without excessively restricting precautions with regard to the presence of light, the temperature and the humidity.

7-(2-(4-(3-(Trifluoromethyl)phenyl)-1,2,3,6-tetrahydropyrid-1-yl)ethyl)isoquinoline besylate exhibits modulating properties with regard to TNF-α. It can therefore be used for the preparation of medicaments, in particular of medicaments intended to treat diseases related to immune or inflammatory disorders.

Such diseases comprise atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glomerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, haemodynamic shock, ischemic pathological conditions (myocardial infarction, myocardial ischaemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage.

Thus, according to another of its aspects, a subject-matter of the invention is medicaments which comprise 7-(2-(4-(3-(trifluoromethyl)phenyl)-1,2,3,6-tetrahydropyrid-1-yl)ethyl)isoquinoline besylate.

These medicaments are used in therapeutics, in particular in the treatment and the prevention of clinical indications related to a deterioration in the immune system or to inflammation or in which inflammatory or immune complications might occur.

Another subject-matter of the invention is thus the use of 7-(2-(4-(3-(trifluoromethyl)phenyl)-1,2,3,6-tetrahydropyrid-1-yl)ethyl)isoquinoline besylate in the preparation of a medicament intended to treat diseases related to immune or inflammatory disorders.

According to another of its aspects, the present invention relates to pharmaceutical compositions comprising, as active principle, 7-(2-(4-(3-(trifluoromethyl)phenyl)-1,2,3,6-tetrahydropyrid-1-yl)ethyl)isoquinoline besylate. These pharmaceutical compositions comprise an effective dose of 7-(2-(4-(3-(trifluoromethyl)phenyl)-1,2,3,6-tetrahydropyrid-1-yl)ethyl)isoquinoline besylate and at least one pharmaceutically acceptable excipient. The said excipients are chosen, according to the pharmaceutical form desired and the method of administration desired, from the usual excipients known to a person skilled in the art.

These pharmaceutical compositions can be presented in any form appropriate for oral, parenteral or intravenous administration, such as tablets, including sugar-coated tablets, capsules, including hard gelatin capsules, suspensions or solutions to be taken orally or to be injected, and the like, in combination with suitable excipients. All these forms advantageously comprise dosages to make possible administration of 1 to 1000 mg per day and per patient, in one or more doses. There may be specific cases where higher or lower dosages are appropriate; such dosages do not depart from the scope of the invention. According to the usual practice, the dosage appropriate to each patient is determined by the physician depending on the method of administration and the weight and the response of the said patient.

By way of example, a unit administration form in the tablet form can comprise the following components:

| | |
|---|---:|
| 7-(2-(4-(3-(Trifluoromethyl)phenyl)-1,2,3,6-tetrahydropyrid-1-yl)ethyl)isoquinoline besylate | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The present invention, according to another of its aspects, also relates to a method for the treatment of clinical pathologies related to inflammation or to a deterioration in the immune system or in which inflammatory or immune complications might occur which comprises the administration, to a patient, of an effective dose of 7-(2-(4-(3-(trifluoromethyl)phenyl)-1,2,3,6-tetrahydropyrid-1-yl)ethyl)isoquinoline besylate.

What is claimed is:

1. 7-(2-(4-(3-(Trifluoromethyl)phenyl)-1,2,3,6-tetra-hydropyrid-1-yl)ethyl)isoquinoline besylate salt.

2. A process for the preparation of 7-(2-(4-(3-(trifluoromethyl)phenyl)-1,2,3,6-tetrahydropyrid-1-yl)ethyl)isoquinoline besylate, comprising reacting 7-(2-(4-(3-(trifluoromethyl)phenyl)-1,2,3,6-tetrahydropyrid-1-yl)ethyl)isoquinoline, in solution in ethanol, with a solution of benzenesulfonic acid in ethanol.

3. A pharmaceutical composition comprising 7-(2-(4-(3-(tri-fluoromethyl)phenyl)-1,2,3,6-tetrahydropyrid-1-yl)ethyl)isoquinoline besylate and at least one pharmaceutically acceptable excipient.

4. A method for the treatment of an immune or inflammatory disorder, the method comprising the administration of a therapeutically effective amount of 7-(2-(4-(3-(trifluoromethyl)phenyl)-1,2,3,6-tetrahydropyrid-1-yl)ethyl)isoquinoline besylate.

5. The method of claim 4 wherein the disorder is rheumatoid arthritis.

6. The method of claim 4 wherein the disorder is cachexia.

* * * * *